United States Patent [19]

Bassin

[11] Patent Number: 5,125,914

[45] Date of Patent: Jun. 30, 1992

[54] CATHETER APPLICATOR PACKAGE

[76] Inventor: Charles S. Bassin, 87 Prinrose Dr., Longmeadow, Mass. 01106

[21] Appl. No.: 594,009

[22] Filed: Oct. 9, 1990

[51] Int. Cl.⁵ ............................................. A61M 31/00
[52] U.S. Cl. ..................................... 604/275; 206/364
[58] Field of Search ............... 604/104, 185, 212, 217, 604/239, 275, 278, 279, 280, 282, 283; 606/197; 206/363, 364

[56] References Cited

U.S. PATENT DOCUMENTS

| 350,105 | 10/1886 | Bennett | 604/278 |
| 655,657 | 8/1900 | Lander | 604/104 |
| 738,009 | 9/1903 | Dews | 604/275 |
| 963,482 | 7/1910 | Stevens | 604/275 |
| 1,546,940 | 7/1925 | Pennington | 604/275 |
| 2,683,456 | 7/1954 | Pierson | 604/278 |
| 2,722,933 | 11/1955 | Allen | 604/275 |
| 4,346,714 | 8/1982 | Child | 604/104 |

Primary Examiner—John D. Yasko
Assistant Examiner—Anthony Gutowski
Attorney, Agent, or Firm—Ross, Ross & Flavin

[57] ABSTRACT

An improved catheter applicator package includes a catheter container or storage cartridge, a dilator separate from the container until usage is desired, and a separate interconnecting tubing ready for connection at one end to the container and at the other end to the dilator as the assemblage is made ready for use.

1 Claim, 1 Drawing Sheet

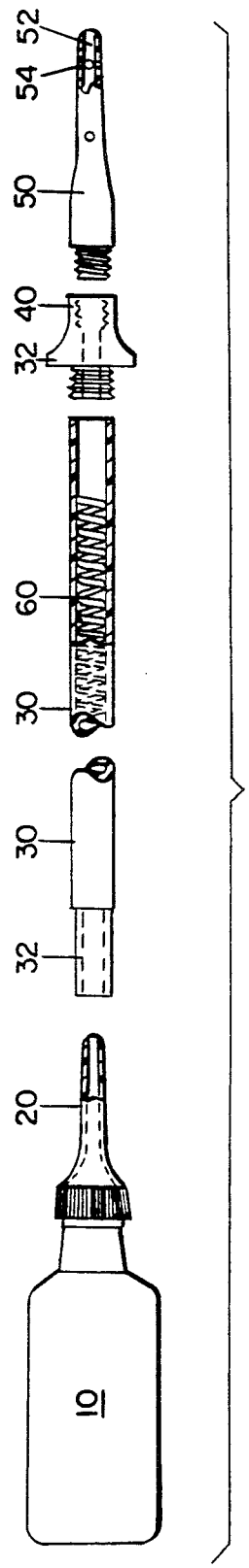
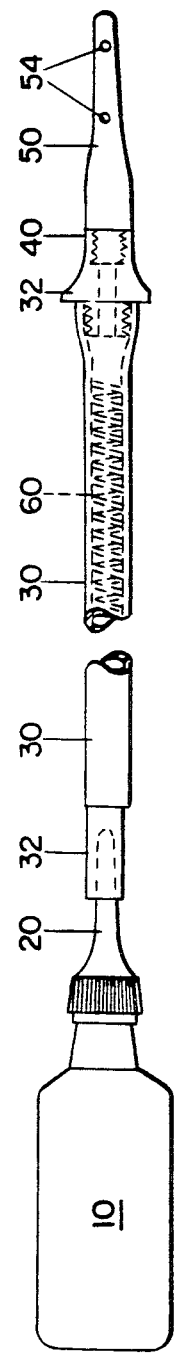
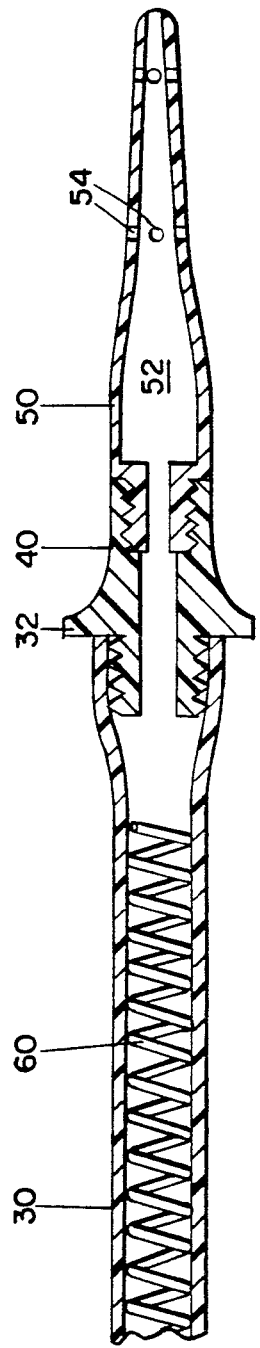

CATHETER APPLICATOR PACKAGE

BACKGROUND OF THE INVENTION

1. Field Of The Invention

My invention relates to medical devices, specifically catheter applicators.

As known, a catheter is a medical device adapted for insertion into a canal, or vessel, or passageway or body cavity and by which a fluid injection into the body is achieved.

It comprehends particularly usages for the purpose of an enema or douche or like purpose wherein a catheter is called into play for association with the posterior opening of the alimentary canal or anus.

2. Description Of The Prior Art

Catheters frequently are inserted without the use of an applicator. Problems arise usually with respect to keeping the area aseptic and more usually with respect to the manipulation of the catheter when and as body insertion is desired.

Known applicators generally require the user to use both hands, one to hold the device and the other to feed the catheter into the anus.

In-as-much as it is necessary to position accurately the catheter with respect to the anus so as to aid in manipulating the applicator, the aid of an assistant sometimes is necessitated.

Vexing problems in maintaining a sterile field at all times and in maintaining a good feel for the procedure in the absence of a view thereof, obviously so as to facilitate catheter insertion, are regularly encountered.

There has been an obvious need for a simple, effective catheter applicator capable of facilitating sterile catheter insertion, providing convenient catheter lubrication, and permitting one-hand advancement and insertion of the device, so that the other hand is free to otherwise assist in holding the fluid supply in an accommodating position of adjacency.

SUMMARY OF THE INVENTION

The catheter-advancing means envisions a package including a hollow container, preferably circular in cross-section, and having a closed rearward end and a front end defining an opening and adapted to permit connection to a resilient catheter tube when preparing for use. Additionally, there is provided a separate semirigid dilator or introducer enclosed throughout substantially the entirety of its length so as to maintain its aseptic integrity prior to and during use.

BRIEF DESCRIPTION OF THE DRAWINGS

FIG. 1 is a broken view in side elevation of the separate components of the invention in non-interconnected relationship;

FIG. 2 is a broken side elevational view of the assembled components in ready-to-use relationship; and FIG. 3 is a sectional view, somewhat enlarged, of the assembled components shown in FIG. 2.

DETAILED DESCRIPTION

The invention envisions a commercially available package in the form of a modified syringe for medicinal purposes inclusive of a container or cartridge for the storage of the fluid or substance intended to be induced into the body, a dilator or introducer, and an interconnecting tube for connecting to both the container and the dilator.

The so-called package for the medicinal preparation includes, as aforesaid, a container or cartridge 10 of flexible material so as to permit its compression in order to expel its contained fluid, and a cap or closure (not shown) of any conventional design and being threadedly engageable with a necked down forward end of the container during storage on the store shelf or preparatory to actual usage by the ultimate consumer.

A separate elongated applicator 20 of a material having some elasticity is capable of being threadedly engaged with container 10 when it is substituted for the closure or cap preparatory to usage.

The applicator has at its outboard end a through passageway leading to an aperture at its outboard end and, of course, communicating with the container interior when interjoined therewith.

Additional to container 10 and cap therefor, and applicator 20, the package which the user will purchase from the customary retailer, will include an elongated tubing 30 having an inboard terminus in the form of a reduced neck 32 having an inner diameter sufficient to receive the outboard terminus of the applicator in a snug-fitting relationship as best shown in FIG. 2.

A fitting 40 having a through opening therethrough is fitted into the outboard terminus of tubing 30 and is provided with a small annular flange 32 which seats against the end face of the tubing.

The fitting is adapted to receive the inner end of a semirigid dilator or introducer 50 fitting and dilator being provided with complementary threads for securing the parts in interengagement.

As aforesaid, the dilator or introducer is separate therefrom in the packaged state, prior to purchase by the ultimate consumer.

A removable sheath (not shown) will be provided closing substantially the length of the dilator to maintain aseptic integrity prior to and during use. The outer surface of the dilator will be provided with a suitable lubricant, for obvious purposes, same to be protected by the sheath until the system is made ready for actual usage.

The dilator is provided with a through end to end channel 52 as well as a number of small interconnecting through holes 54 at points along the dilator sidewall.

Within tube 30 a flexible compression spring 60 is disposed so as to lie in adjacency to fitting 40, which spring serves to preclude any sharp bending of the tubing, such bending being desirably precluded so as to allow the free flow of liquid therethrough when in use.

The components, in each case, may be made from a plastic or rubber or equivalent material.

It will be understood that the container is at least partly filled with a suitable fluid before use of the applicator.

The dilator is used by first grasping it in one hand with the finger or fingers pressing against the annular flange for guiding the dilator into the body cavity, while the other hand of the user is holding the container, all whereby, with one hand the user is enabled to facilitate proximation of the dilator toward and into the anus.

When the dilator has been fully advanced to the desired anatomical location, the container may then be squeezed so as to expel the fluid therewithin through the tube and dilator and into the body.

Accordingly, an improved catheter applicator is provided which can be fabricated inexpensively but which provides a number of advancements over the usual types of catheter applicators.

Thus, the applicator facilitates easier and less uncomfortable catheter insertion by one user while aiding in preserving the sterile field so as to minimize danger of infection.

Various changes, modifications, substitutions and the like can be made in the improved applicator of the invention and the components thereof. All such changes, modifications and substitutions as are within the scope of the appended claims form a part of the present invention.

I claim:

1. In a medical device, a package of catheter applicator components sold to a consumer in unassembled form ready for quick and easy assemblage by the consumer prior to usage comprising:

a compressible storage container for storing a medicament fluid intended to be introduced into the body of the consumer and having a necked-down threaded exit opening at a forward end thereof and a threaded cap for closing the exit opening during storage, a closure having a through passageway and being threadedly engageable at its rearward end with the necked down exit opening of the container during operational usage, a tapered dilator for insertion into a body cavity of the consumer in operational usage and having a through end-to-end channel and a series of interconnecting radially-extending through openings in the side wall thereof and an externally threaded rearwardly facing inboard end, an interconnecting elongated resilient tubing having outboard and inboard termini with the inboard terminus being in the form of a reduced neck for snugly receiving in sleeved relationship the outboard end of the closure, a fitting having a through end-to-end channel and an internally threaded forward end for threaded engagement with the rearwardly facing inboard end of the dilator and an externally threaded rearward end for snugly receiving in sleeved relationship the outboard end of the tubing, and a flexible compression spring sleeved within the tubing for the preclusion of sharp bending of the tubing, the tubing serving for facilitating connecting communication between the contents of the container and the discharge end of the dilator during operational usage.

* * * * *